United States Patent [19]

Lamatsch et al.

[11] Patent Number: 5,672,716
[45] Date of Patent: Sep. 30, 1997

[54] YELLOW DIKETOPYRROLOPYRROLE PIGMENTS

[75] Inventors: Bernd Lamatsch; Olof Wallquist, both of Marly; Ingo Schlöder, Matran, all of Switzerland

[73] Assignee: Ciba-Geigy Corporation, Tarrytown, N.Y.

[21] Appl. No.: 551,192

[22] Filed: Oct. 31, 1995

[30] Foreign Application Priority Data

Nov. 4, 1994 [CH] Switzerland ............... 3305/94

[51] Int. Cl.$^6$ .............................. C07D 487/04
[52] U.S. Cl. .............................. 548/453
[58] Field of Search .............................. 548/453

[56] References Cited

U.S. PATENT DOCUMENTS

| | | | |
|---|---|---|---|
| 4,415,685 | 11/1983 | Iqbal et al. | 524/92 |
| 4,579,949 | 4/1986 | Rochat et al. | 546/167 |
| 4,720,305 | 1/1988 | Iqbal et al. | 106/288 |
| 4,783,540 | 11/1988 | Babler | 548/453 |
| 4,810,802 | 3/1989 | Wallquist et al. | 548/453 |
| 5,200,528 | 4/1993 | Wooden et al. | 548/453 |
| 5,354,869 | 10/1994 | Langhals et al. | 548/453 |

Primary Examiner—Patricia L. Morris
Attorney, Agent, or Firm—Michele Kovaleski

[57] ABSTRACT

The invention relates to diketopyrrolo[3,4-c]pyrroles of formula

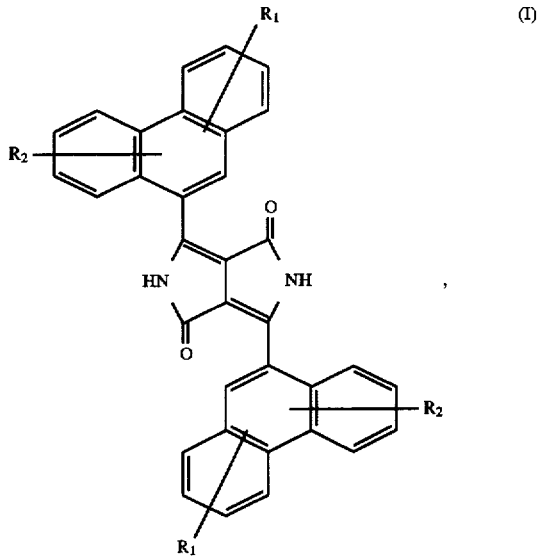

(I)

wherein $R_1$ and $R_2$ are each independently of the other hydrogen, halogen, $C_1$–$C_6$alkyl, cyano or a —$OR_3$, —$COOR_3$, —$CON(R_3)(R_4)$, —$COR_3$ or —$N(R_3)(R_4)$ group, and $R_3$ and $R_4$ are each independently of the other hydrogen, $C_1$–$C_6$alkyl, phenyl which is unsubstituted or substituted by halogen or $C_1$–$C_6$alkyl.

Said diketopyrrolo[3,4-c]pyrroles are pigments colored in a strong yellow shade having good fastness properties.

3 Claims, No Drawings

YELLOW DIKETOPYRROLOPYRROLE PIGMENTS

The present invention relates to novel yellow diketopyrrolopyrroles and to the use thereof as pigments.

1,4-Diketopyrrolo[3,4-c]pyrroles have been known for some years as red pigments having excellent pigment properties. U.S. Pat. No. 4,415,685, inter alia, discloses diketopyrrolopyrroles of formula

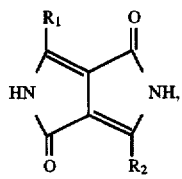

wherein $R_1$ and $R_2$ are isocyclic or heterocyclic radicals, preferably mono- to tetracyclic, more particularly mono- or bicyclic radicals, as red pigments having superior chroma, excellent colour strength and good fastness to e.g. light, weathering, heat and migration. The superior suitability of such products as pigments of orange to, preferably, red shade, is also confirmed in numerous follow-up patents such as, inter alia, in U.S. Pat. No. 4,579,949, U.S. Pat. No. 4,720,305, U.S. Pat. No. 4,810,802, U.S. Pat. No. 4,783,540, U.S. Pat. No. 5,200,528 and others more.

Entirely surprisingly, it has now been found that the diketopyrrolopyrroles of the above formula, wherein the isocyclic radicals are unsubstituted or substituted phenanthren-9-yl, are yellow pigments which likewise have excellent pigment properties.

Accordingly, the invention relates to diketopyrrolo[3,4-c]pyrroles of formula

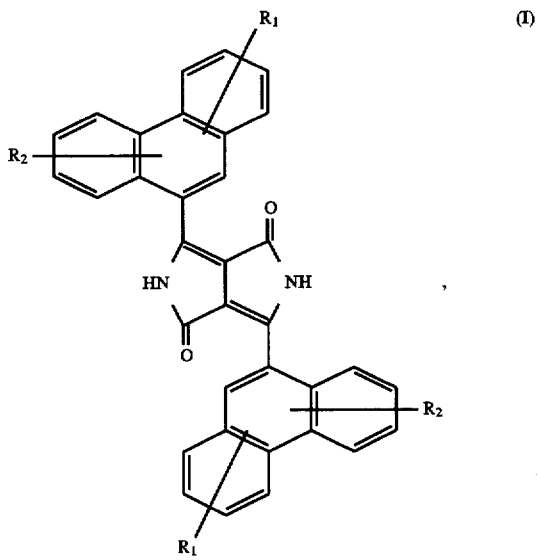

wherein $R_1$ and $R_2$ are each independently of the other hydrogen, halogen, $C_1$–$C_6$alkyl, cyano or a —$OR_3$, —$COOR_3$, —$CON(R_3)(R_4)$, —$COR_3$ or —$N(R_3)(R_4)$ group, and $R_3$ and $R_4$ are each independently of the other hydrogen, $C_1$–$C_6$alkyl, phenyl which is unsubstituted or substituted by halogen or $C_1$–$C_6$alkyl.

Halogen substituents are typically iodo, bromo, fluoro or, preferably, chloro.

$C_1$–$C_6$Alkyl is typically methyl, ethyl, n-propyl, isopropyl, n-butyl, sec-butyl, tert-butyl, n-pentyl, tert-amyl or n-hexyl.

Particularly interesting are the novel 1,4-diketopyrrolo[3,4-c]pyrroles of formula I, wherein $R_1$ is hydrogen, chloro, bromo, methyl, cyano, —$N(R_3)_2$ or —$OR_3$, $R_2$ is hydrogen, and $R_3$ is hydrogen or methyl.

Preferred pigments are those novel pigments of formula I, wherein $R_1$ and $R_2$ are hydrogen. Preferred substituent positions are the 2-, 3-, 6- and 7-position at the phenanthryl system.

The novel diketopyrrolo[3,4-c]pyrroles of formula I can be prepared in general accordance with standard known processes, typically by reacting a diester succinate with a nitrile of formula

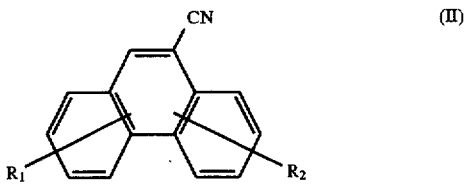

in the requisite ratios such as disclosed, inter alia, in U.S. Pat. No. 4,579,949.

The nitriles of formula II are known compounds. Should any of them still be novel, they can be prepared in general accordance with standard known methods.

The novel diketopyrrolo[3,4-c]pyrroles can be used as pigments for colouring organic material of high molecular weight.

Illustrative examples of high molecular weight organic materials which can be coloured with the novel diketopyrrolo[3,4-c]pyrroles are cellulose ethers and esters, typically ethyl cellulose, nitro cellulose, cellulose acetate, cellulose butyrate, natural resins or synthetic resins, typically polymerisation or condensation resins, such as aminoplasts, preferably urea/formaldehyde and melamine/formaldehyde resins, alkyld resins, phenoplasts, polycarbonates, polyolefins, polystyrene, polyvinyl chloride, polytetrafluoro ethylene, polyamides, polyurethanes, polyester, polyether ketones, polyphenylenoxides, rubber, casein, silicone and silicone resins, singly or in mixtures.

The above high molecular weight organic compounds may be obtained singly or as mixtures as plastics, melts or in the form of spinning solutions, paints, coating materials or printing inks. Depending on the end use requirements, it is expedient to use the diketopyrrolo[3,4-c]pyrroles of this invention as toners or in the form of preparations. The novel diketopyrrolo[3,4-c]pyrroles may be used in an amount of 0.01 to 30% by weight, preferably of 0.1 to 10% by weight, based on the high molecular weight organic material to be pigmented.

For pigmenting paints and printing inks, the high molecular weight organic materials and the novel diketopyrrolo[3,4-c]pyrroles, together with optional additives such as fillers, other pigments, siccatives or plasticisers, are finely dispersed or dissolved in a common organic solvent or solvent mixture. The procedure may be such that the individual components by themselves, or also several jointly, are dispersed or dissolved in the solvent and thereafter all the components are mixed.

The colourings obtained e.g. in plastics, fibres, paints or prints, have good allround properties, such as superior colour strength, excellent dispersibility, good fastness to migration, heat, light and weathering as well as good hiding power and good gloss.

The invention is illustrated by the following Examples.

EXAMPLE 1

48 ml of a 25% solution of potassium tert-amylate in toluene are added to 20 ml of tert-amyl alcohol. After heating to 87° C. (temperature in the vessel), 10.2 g of 9-cyanophenanthrene are added, and over 25 minutes 7.6 ml of diisopropyl succinated are added dropwise. The mixture is stirred for 4 hours at this temperature. With vigorous stirring with a toothed disc, the suspension so obtained is added to a mixture of 200 ml of water, 200 ml of methanol and 3 ml of acetic acid and then stirred for a further 10 minutes. The mixture is filtered and the filter product is washed with methanol and water and dried at 60° C. under vacuum, to give 2.3 g (19% of theory) of the yellow pigment of formula

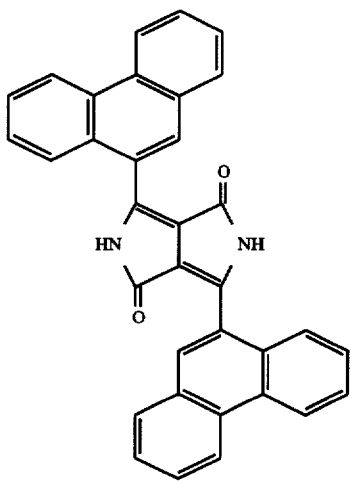

EXAMPLE 2

A mixture of 1.0 g of the pigment obtained in Example 1, 1.0 g of antioxidant (IRGANOX® 1010, CIBA-GEIGY AG) and 1000 g of polyethylene-HD granulate (®VESTOLEN 60-16, HUELS) is premixed for 15 minutes in a glass flask on a roller gear table. The mixture is then extruded in two passes in a single screw extruder. The granulate so obtained is moulded to plates at 220° C. in an injection moulding machine (Allround Aarburg 200) and then post-formed for 5 minutes at 180° C. The mouldings are coloured in a strong yellow shade of good fastness properties.

EXAMPLE 3

0.6 g of the pigment obtained in Example 1 are mixed with 67 g of polyvinyl chloride, 33 g of dioctylphthalate, 2 g of dibutyl tin dilaurate and 2 g of titanium dioxide and processed on a roll mill for 15 minutes at 160° C. to a thin sheet. The yellow PVC sheet so obtained is coloured strongly and is stable to light.

EXAMPLE 4

2 g of the product obtained according to Example 1 and 48 g of a stoving lacquer comprising 56 g of alkyd resin ALKYDAL® F310 (Bayer AG; 60% in xylene)

13 g of melamine resin CYMEL® 327 (cyanamide; 90% in butanol)

25 g of xylene 25 g of butanol 2.5 g of 1-methoxy-2-propanol, and 1 g of silicone oil (1% in xylene)

are mixed by conventional methods. The resultant colour lake is drawn to a film on a glass plate. Before storing in a circulating air oven (30 minutes at 120° C.), the colour lake is allowed to dry in the air for c. 30 minutes at an inclination of 25°.

A lacquer coloured in a strong yellow shade is obtained having good allround fastness properties.

What is claimed is:

1. A diketopyrrolo[3,4-c]pyrrole of formula

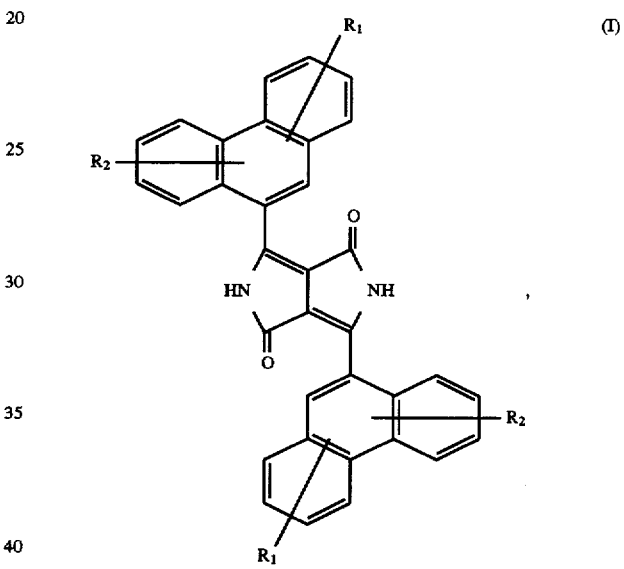

wherein $R_1$ and $R_2$ are each independently of the other hydrogen, halogen, $C_1$–$C_6$alkyl, cyano or a —$OR_3$, —$COOR_3$, —$CON(R_3)(R_4)$, —$COR_3$ or —$N(R_3)(R_4)$ group, and $R_3$ and $R_4$ are each independently of the other hydrogen, $C_1$–$C_6$alkyl, phenyl which is unsubstituted or substituted by halogen or $C_1$–$C_6$alkyl.

2. A diketopyrrolo[3,4-c]pyrrole of formula I as claimed in claim 1, wherein $R_1$ is hydrogen, chloro, bromo, methyl, cyano, —$N(R_3)_2$ or —$OR_3$, $R_2$ is hydrogen, and $R_3$ is hydrogen or methyl.

3. A diketopyrrolo[3,4-c]pyrrole of formula I as claimed in claim 1, wherein $R_1$ and $R_2$ are hydrogen.

* * * * *